Aug. 8, 1967 R. M. MILFELD Plant Pat. 2,757
AZALEA PLANT
Filed April 15, 1966
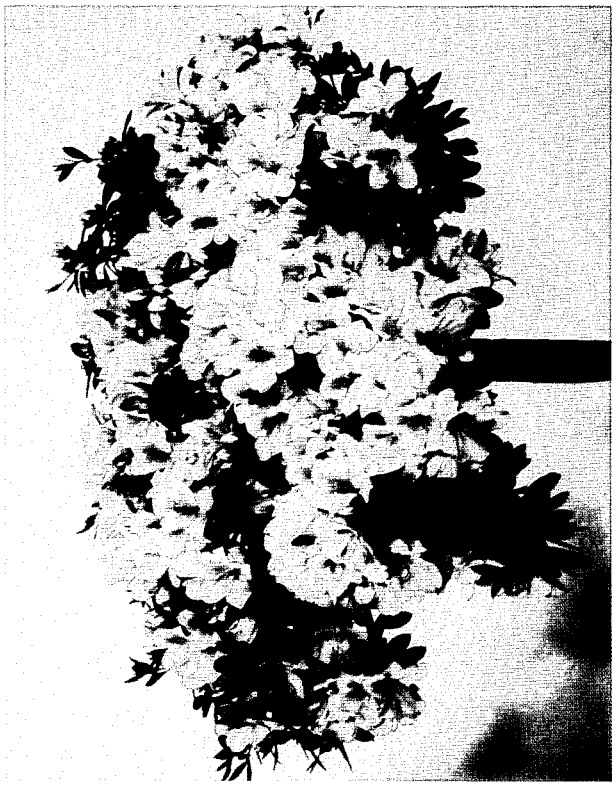
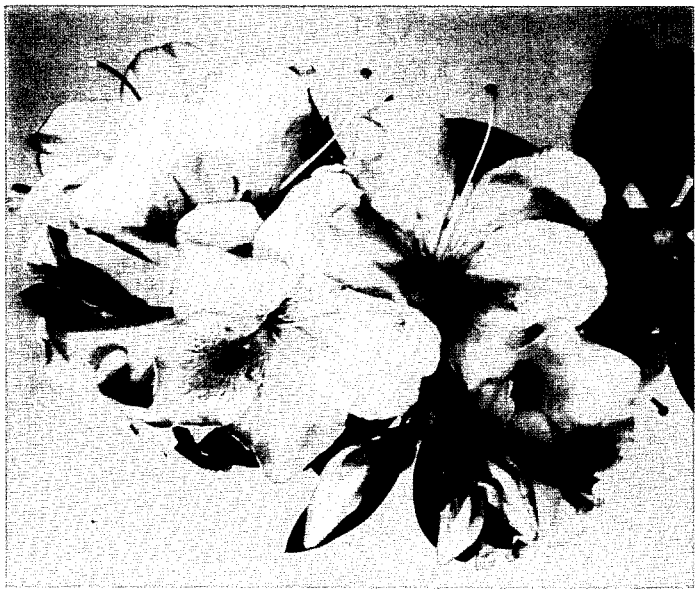
Inventor.
R. M. Milfeld
By: Robb & Robb
Attorneys.

United States Patent Office

Plant Pat. 2,757
Patented Aug. 8, 1967

2,757
AZALEA PLANT

Raymond M. Milfeld, Monrovia, Calif., assignor to Milfeld's Nursery, Monrovia, Calif., a co-partnership Filed Apr. 15, 1966, Ser. No. 542,976
1 Claim. (Cl. Plt.—55)

The present invention relates to a new and distinct variety of azalea plant of the Indian azalea type, which was discovered by me as a sport of the azalea variety known as "Duc De Rohan" (unpatented).

At the time of my discovery aforementioned, a block of plants of the variety "Duc De Rohan" were being grown commercially under my direction and control in the nursery of my assignee, located at Monrovia, Calif. and in which I held and still hold a partnership interest. In the course of tending these plants and selecting plants from this block for sale, my attention was attracted to one particular plant among this block which bore flowers of a variegated light pink and white color substantially different from the normally darker salmon pink flower color of the parent variety "Duc De Rohan." Upon close inspection of this particular plant, I found that it had sported, and thereupon took prompt steps to preserve the sport, keep it under observation, and to propagate the same from cuttings taken therefrom, as performed by me in the nursery aforesaid. Continued observations and tests of the original sport and the progeny thereof confirmed that the flower color characteristics referred to in the foregoing are fixed and come true by asexual reproduction, while the new variety otherwise conforms substantially to the parent variety. Thus, the new variety represents a new and unique combination of characteristics which distinguish it from its parent, as well as from all other azalea varieties of which I am aware, as evidenced by having substantially the same compact habit of growth, hardiness, foliage color and good disease resistance as the variety "Duc De Rohan," but bearing distinctive and attractive flowers which are light pink in color, with variegated white edges and a deeper speckled pink white throat.

The accompanying drawing shows a typical specimen plant of my new azalea variety, as well as typical specimen blooms thereof on an enlarged scale and in different stages of development, all as depicted in color as nearly true as it is reasonably possible to make the same in a color illustration of this character.

The following is a detailed description of the new variety, with color terminology in accordance with Wilson's Colour Chart published by the British Colour Council in collaboration with the Royal Horticultural Society, except where general color terms of ordinary dictionary significance are obvious:

Locality where grown and observed: In foothills of San Gabriel Valley, Calif.

Parentage: Sport of "Duc De Rohan."

Propagation: Holds its distinguishing characteristics through succeeding propagations by cuttings.

Plant:

*Form.*— Bush; much-branched.

*Habit.*—Vigorous; branching.

*Blooming habit.*—Very prolific.

*Blooming season.*—From February to April; suitable for forcing.

*Foliage.* — Size — medium. Quantity — abundant. Color: New foliage—upper side—Spinach Green, Plate 0960/2; under side Spinach Green, Plate 0960/1. Old foliage—upper side—Spinach Green, Plate 0960; under side Spinach Green, Plate 0960/2. Shape—oval pointed. Texture: upper side—glossy; corrugated; under side rough. Margin—entire; even edge with light hairs. Aspect—oval pointed, with center vein running entire length and having lateral veins extending therefrom. Disease resistance—no evidence of any diseases to which azalea varieties are normally susceptible, as determined by comparison with other varieties grown under comparable conditions at Monrovia, Calif.

Flower:

*Borne.*—3 or 4 to stem; in regular clusters; on strong, short stems.

*Quantity.*—Abundant, both outdoors and in greenhouse.

*Continuity.*—One season; spring of every year.

*Petalage.*—Number of petals under normal conditions—5. Texture: inside—velvety; outside smooth. Appearance: inside—light pink, with deep rose throat and variegated white edge, with pink colors ranging from Rose Opal, Plate 022/3 to Rose Opal, Plate 022/1 in throat; outside—Rose Opal, Plate 022/3, with variegated white edge; flower tends to lighten as it ages. Shape—trumpet. Arrangement—3 petals at top and 2 petals at bottom.

Bud: Long tapered. Color—Rose Opal, Plate 022/3, with small amount of variegated white edge.

Reproductive organs:

*Stamens.*—Color—light pink, lightening at base to white.

*Pollen.*—Color—light amber.

*Styles.*—8 or 9 small stamens, with one extra long style in center.

*Ovaries.*—5 apple green petals and grayish green seed pod.

General observations: The new variety is substantially the same as the parent variety in respect to its compact habit of growth, hardiness, foliage color and good disease resistance, while being the only true variegated light pink azalea of the Indian type available in southern California.

I claim:

A new and distinct variety of azalea plant of the Indian type, substantially as herein shown and described, characterized particularly as to novelty by the unique combination of compact habit of growth, hardiness, foliage color and good disease resistance comparable to the parent variety "Duc De Rohan" (unpatented), but which bears distinctive and attractive flowers that are substantially darker in color than those of the parent variety aforesaid, and which are light pink in color, with variegated white edges and have a deeper speckled pink throat.

No references cited.

ABRAHAM G. STONE, *Primary Examiner.*

ROBERT E. BAGWILL, *Examiner.*